(12) United States Patent
Matsumoto et al.

(10) Patent No.: US 6,407,298 B1
(45) Date of Patent: Jun. 18, 2002

(54) PROCESS FOR THE PREPARATION OF (P-CHLOROPHENYL)PROPANOL DERIVATIVES

(75) Inventors: Hiroo Matsumoto; Minako Kamikawaji; Takashi Horiuchi, all of Chiba (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 09/830,555

(22) PCT Filed: Nov. 29, 1999

(86) PCT No.: PCT/JP99/06654

§ 371 (c)(1),
(2), (4) Date: May 4, 2001

(87) PCT Pub. No.: WO00/35843

PCT Pub. Date: Jun. 22, 2000

(30) Foreign Application Priority Data

Dec. 11, 1998 (JP) ............................................. 10-352529

(51) Int. Cl.$^7$ .............................................. C07C 17/16
(52) U.S. Cl. ........................ 570/191; 568/812; 570/185
(58) Field of Search ................................. 568/812, 814, 568/436, 437; 570/185, 191

(56) References Cited

U.S. PATENT DOCUMENTS

| | | | |
|---|---|---|---|
| 2,184,526 A | * | 12/1939 | Meuly |
| 3,487,116 A | * | 12/1969 | Rylander |
| 3,663,626 A | * | 5/1972 | Arrigo |
| 4,070,374 A | * | 1/1978 | Chalk |
| 4,486,607 A | * | 12/1984 | Webb |
| 4,590,281 A | * | 5/1986 | Yamazaki |
| 6,288,120 B1 | * | 9/2001 | Carmeron |

FOREIGN PATENT DOCUMENTS

| | | |
|---|---|---|
| DE | 299 186 | 4/1992 |
| FR | 2 623 798 | 6/1989 |
| GB | 1 455 766 | 11/1976 |
| JP | 55-81831 | 6/1980 |

OTHER PUBLICATIONS

Bott, J. Chem. Soc., pp. 1548–1553 (1964).*
J. Chem. Soc., Chem. Commun., 1984, pp. 1287–1289.
Journal of the Chemical Society, No. 19, pp. 1287–1289, "Palladium–Catalysed Vinylation of Organic Halides Under Solid–Liquid Phase Transfer Conditions", Oct. 1, 1984, Jeffrey.

* cited by examiner

*Primary Examiner*—Michael L. Shippen
(74) *Attorney, Agent, or Firm*—Oblon, Spivak, McClelland, Maier & Neustadt, P.C.

(57) ABSTRACT

A process for the preparation of an alcohol compound (1), characterized by subjecting p-iodochlorobenzene to Pd coupling with allyl alcohol in the presence of tetramethylammonium chloride, followed by reduction, and a process for the preparation of a compound (2), characterized by brominating the alcohol compound (1) obtainable by said process:

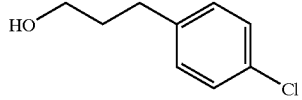

[1]

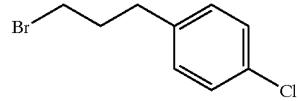

[2]

22 Claims, No Drawings

PROCESS FOR THE PREPARATION OF (P-CHLOROPHENYL)PROPANOL DERIVATIVES

TECHNICAL FIELD

The present invention relates to a process for the preparation of a (p-chlorophenyl)propanol derivative which can be a useful intermediate for an antiplatelet.

BACKGROUND ART

The compound represented by the formula (3) is a compound useful as an antiplatelet, as disclosed in JP-B-7-107055, EP 482208A and U.S. Pat. No. 5,314,883.

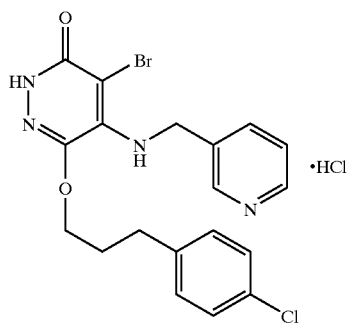

[3]

The process for the preparation of the compound (3) as disclosed in the above patents, comprises condensing a compound (2) with a compound (4), and further reacting 3-picolylamine thereto, followed by conversion to a hydrochloride, as shown in Scheme 1.

Scheme 1

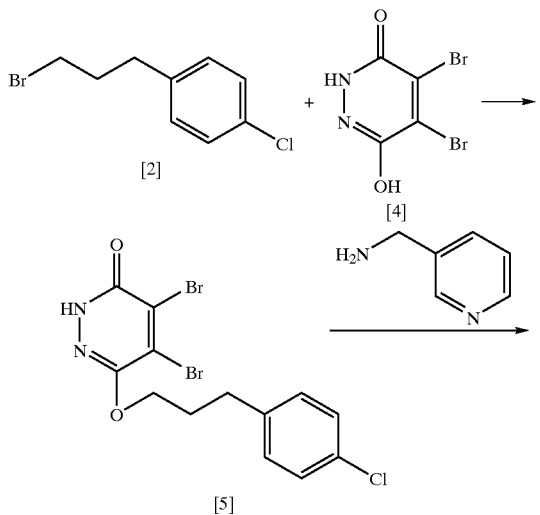

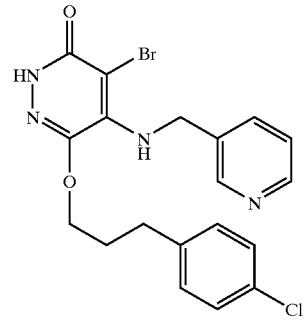

[6]

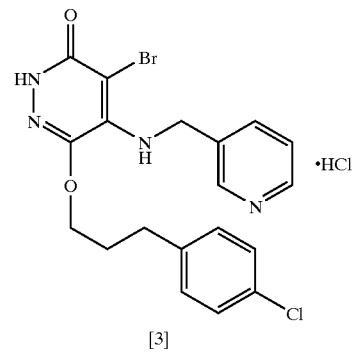

[3]

In order to obtain this bromine compound (2) initially, the production was carried out by a process via a p-chlorocinnamate derivative, as shown in Scheme 2, but it was difficult to suppress a dechlorination reaction during the hydrogenation of the double bond.

Scheme 2

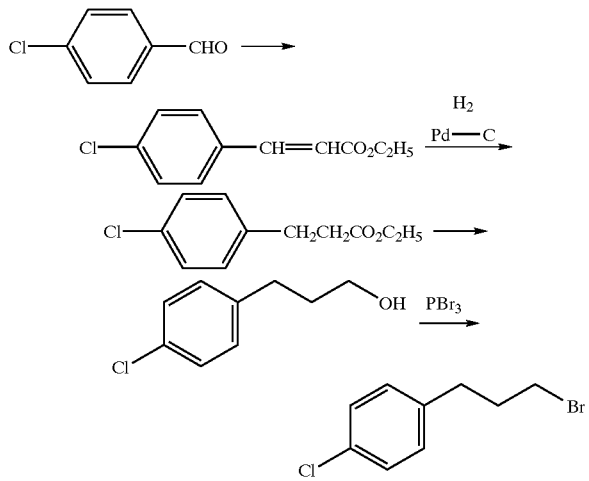

Then, we paid attention to a reaction for synthesizing a compound (7) by subjecting p-iodochlorobenzene and allyl alcohol to Pd coupling at a relatively low temperature in the presence of a quaternary ammonium salt having a relatively large alkyl group such as tetrabutylammonium chloride, as reported in J.C.S. in 1984 (J. Chem. Soc. Commun., 1984, 19, 1287–1289), because if this compound is reduced, the required alcohol compound can easily be obtained. However, according to the reaction conditions disclosed in this literature, the amount of palladium acetate to be used is relatively large at a level of from 1 to 2 mol %, and the quaternary ammonium salt is expensive and has a large molecular weight. Therefore, this process was considered to be not proper as an industrial process (in the same literature, a study was made on the types of quaternary ammonium salts, and as a result, tetrabutylammonium chloride was selected). Further, inclusion of a branched isomer (compound (8)) and its reduced form (9) formed in an amount of a few %, was also a problem which must have been solved.

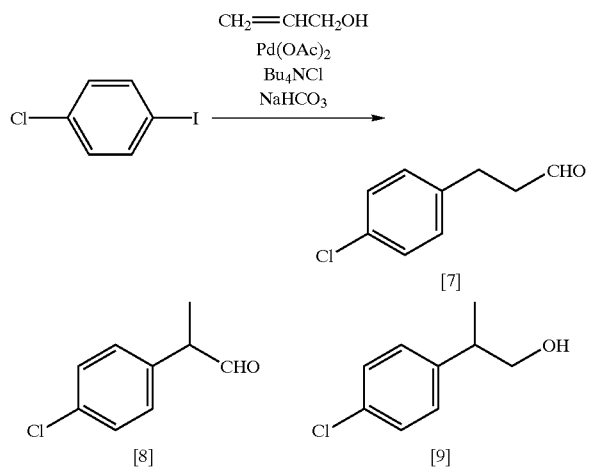

DISCLOSURE OF THE INVENTION

In the course of a strenuous study, we have found that if the quaternary ammonium salt is changed to tetramethylammmonium chloride without changing other conditions disclosed in the literature, although the reaction rate is very slow (reaction temperature: room temperature), when the reaction temperature is raised to at least 50° C., the desired reaction will proceed very efficiently. As a result, the amount of palladium acetate to be used may be sufficient even at a level of 0.1 mol %. By this reaction, the above-mentioned branched isomer will be formed in an amount of about 6%, but it has been found that if bromination is carried out as it stands, to obtain a compound (2), and the condensation with the compound (4) is carried out, the branched bromine compound will be dehydrobrominated by the base and will not react with the compound (4). Namely, the branched isomer formed by the Pd coupling, requires no special separation operation.

Further, the aldehyde intermediate as the coupling product may be isolated, and its structure has already been identified. However, it has been experimentally confirmed that it may be subjected to the next reaction without isolating it. Namely, simply by adding sodium borohydride to the reaction solution after confirming the progress of coupling, it may be led to the alcohol compound (1).

Namely, the present invention relates to a process for the preparation of an intermediate of a pyridazinone (formula (3)), characterized by subjecting p-iodochlorobenzene to Pd coupling with ally alcohol in the presence of tetramethylammonium chloride, followed by reduction to obtain an alcohol compound (1), which is further brominated to a compound (2).

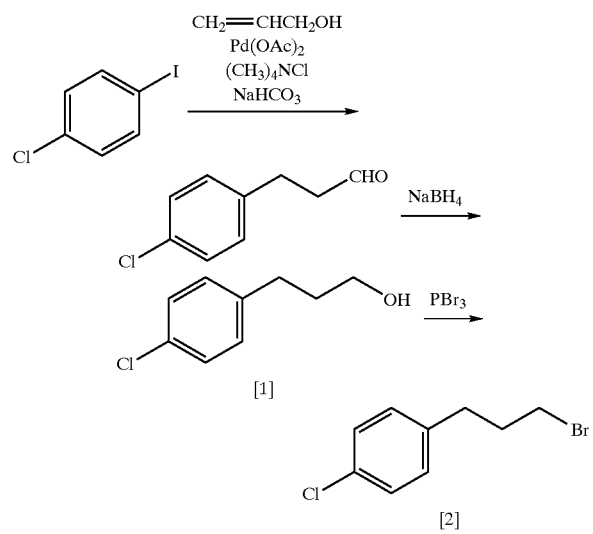

BEST MODE FOR CARRYING OUT THE INVENTION

Process for the preparation of compound (1) (Pd coupling reaction and reduction)

The solvent to be used for the reaction is preferably of an amide type such as dimethylformamide, dimethylacetamide, N-methylpyrrolidone or dimethylimidazolidinone, and it may be used alone or as mixed with e.g. an aromatic hydrocarbon such as toluene or xylene. It is a feature of the present invention to use tetramethylammonium chloride which is most inexpensive and has a small molecular weight (i.e. the amount to be used, being small), as a quaternary ammonium salt, and the amount to be used, is within a range of from 0.5 to 3 times by mol, preferably from 0.9 to 1.5 times by mol. It is also a feature of the present invention that the amount of palladium acetate as the catalyst may be reduced and is within a range of from 0.01 to 0.2 mol %, preferably within a range of from 0.05 to 0.15 mol %. As the base, sodium hydrogencarbonate or sodium carbonate is required, and the amount to be used is within a range of from an equimolar amount to 20 times by mol, preferably within a range of from 3 to 10 times by mol. The reaction temperature is within a range of from 50 to 150° C., preferably within a range of from 50 to 100° C.

The aldehyde compound may be extracted with ethyl acetate or toluene after distilling the solvent off, and may be isolated as an intermediate. However, it is preferred to carry out the reduction of the next step as it stands without isolating it. Namely, after confirming the formation of the aldehyde intermediate by gas chromatogram, the reaction solution is cooled to −20 to 10° C., and from 0.25 to 1 time by mol, preferably from 0.25 to 0.35 time by mol, of sodium borohydride is added, whereby the reduction of the aldehyde can be carried out within a reaction time of one hour.

Process for the Preparation of Compound (2) (Bromination Reaction)

Using an aromatic hydrocarbon solvent such as toluene or xylene, bromination of the alcohol compound (1) can be carried out with phosphorus tribromide. The amount of phosphorus tribromide to be used, is from 0.3 to 2 times by mol, preferably from 0.5 to 1.2 times by mol, and the reaction temperature is within a range of from 50 to 150° C.

The process for the preparation of a (p-chlorpheny) propanol derivative according to the present invention is an efficient process, whereby a dechlorination reaction which takes place in the conventional process, is not observed. Further, the amount of palladium acetate used during the coupling, was not more than 1/10.

Now, the present invention will be described in detail with reference to Examples, but the present invention is by no means restricted by these Examples.

EXAMPLE 1

Pd Coupling Reaction and Reduction of Aldehyde 95.38 g (400 mmol) of p-chloroiodobenzene, 34.85 g (600 mmol) of ally alcohol, 0.089 g (0.4 mmol) of palladium acetate and 47.99 g (2,000 mmol) of sodium hydrogencarbonate, were added to 200 ml of dimethylformamide (DMF), followed by heating until the internal temperature of the suspension became 50° C. The heating was continued for 7 hours, and after confirming the formation of the aldehyde compound by gas chromatogram, the suspension was cooled to 5° C. Then, 4.54 g (120 mmol) of sodium borohydride was added, followed by stirring for 30 minutes. Then, 100 ml of a saturated ammonium chloride aqueous solution, 100 ml of water and 200 ml of toluene were added, followed by stirring for one hour. After removing insolubles by Celite filtration, liquid separation was carried out, and the water layer was extracted again with 200 ml of toluene. The tolune layers were put together, concentrated and then distilled (107° C./1 mmHg) to obtain 63.4 g (y 93%) of 3-(p-chlorophenyl)-1-propanol {compound (1)} as a colorless oily substance. From the analysis by gas chromatography, this product was found to contain 6% of the branched isomer.

EXAMPLE 2

Bromination 66.0 g (387 mmol) of 3-(p-chlorophenyl)-1-propanol was dissolved in 350 ml of toluene, and a solution having 105 g (387 mmol) of phosphorus tribromide dissolved in 50 ml of toluene, was dropwise added thereto. After the dropwise addition, the internal temperature of the reaction solution was raised to 90° C. and returned to room temperature 3 hours later. 250 ml of a 1N sodium hydroxide aqueous solution was added thereto, followed by shaking. Then, the solution was left to stand still for liquid separation, and the water layer was extracted again with 150 ml of toluene. The toluene layers were put together and washed with 150 ml of a saturated sodium chloride aqueous solution, followed by Celite filtration, and then the solvent was distilled off. The residue was Idistilled to obtain 75.2 g (y 83%) of the desired 3-(p-chlorophenyl)-1-propyl bromide {compound (2)) as a colorless oily substance (85–89° C./0.3 mmHg)

REFERENCE EXAMPLE (Pd Coupling Reaction)

11.9 g (0.05 mol) of p-chloroiodobenzene was dissolved in 25 ml of dimethylformamide, and 4.36 g (0.075 mol) of allyl alcohol, 6.54 g (0.06 mol) of tetramethylammonium chloride, 21.0 g (0.25 mol) of sodium hydrogencarbonate and 225 g (2 mol %) of palladium acetate were added thereto, followed by stirring at room temperature. Six hours later, the product was analyzed by gas chromatography, whereby p-chloroiodobenzene was 95.5%, and 3-(p-chlorophenyl)-1-propanal was 3.8%. The product was left to stand for 10 days, whereupon p-chloroiodobenzene was 3.70%, and 3-(p-chlorophenyl)-1-propanal was 88.4%.

What is claimed is:

1. A process for the preparation of an alcohol compound (1), characterized by subjecting p-iodochlorobenzene to Pd coupling with allyl alcohol in the presence of tetramethylammonium chloride, followed by reduction:

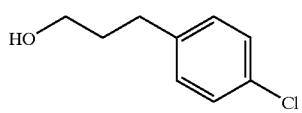

[1]

2. A process for preparing a compound (2), comprising subjecting p-iodochlorobenzene to Pd coupling with allyl alcohol in the presence of tetramethylammonium chloride, followed by reduction to yield an alcohol compound (1):

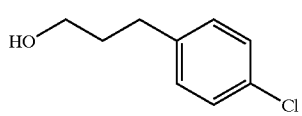

[1]

and brominating the alcohol compound (1) to produce a compound (2)

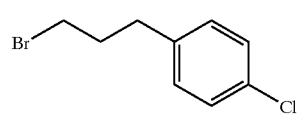

[2]

3. The process of claim 1, wherein said Pd coupling comprises contacting said p-iodochlorobenzene with palladium acetate.

4. The process of claim 3, wherein said palladium acetate is in an amount from 0.01 to 0.2 mol %.

5. The process of claim 3, wherein said palladium acetate is in an amount from 0.05 to 0.15 mol %.

6. The process of claim 1, wherein said tetramethylammonium chloride is in amount from 0.5 to 3 times by mol.

7. The process of claim 1, wherein said tetramethylammonium choloride is in an amount from 0.9 to 1.5 times by mol.

8. The process of claim 1, which is performed at a temperature from 50 to 150° C.

9. The process of claim 1, which is performed at a temperature from 50 to 100° C.

10. The process of claim 1, wherein said reduction comprises adding sodium hydrogencarbonate or sodium carbonate.

11. The process of claim 2, wherein said brominating comprise contacting the alcohol compound (1) with phosphorous tribromide.

12. The process of claim 11, wherein said phosphorous tribromide is in an amount from 0.3 to 2 times by mol.

13. The process of claim 11, wherein said phosphorous tribromide is in an amount from 0.5 to 1.2 times by mol.

14. The process of claim 2, wherein said brominating is performed at a temperature of from 50 to 150° C.

15. The process of claim 2, wherein said Pd coupling comprises contacting said p-iodochlorobenzene with palladium acetate.

16. The process of claim 15, wherein said palladium acetate is in an amount from 0.01 to 0.2 mol %.

17. The process of claim 15, wherein said palladium acetate is in an amount from 0.05 to 0.15 mol %.

18. The process of claim 2, wherein said tetramethylammonium chloride is in amount from 0.5 to 3 times by mol.

19. The process of claim 2, wherein said tetramethylammonium choloride is in an amount from 0.9 to 1.5 times by mol.

20. The process of claim 2, which is performed at a temperature from 50 to 150° C.

21. The process of claim 2, which is performed at a temperature from 50 to 100° C.

22. The process of claim 2, wherein said reduction comprises adding sodium hydrogencarbonate or sodium carbonate.

* * * * *